(12) United States Patent
Soltanian et al.

(10) Patent No.: US 11,400,944 B2
(45) Date of Patent: Aug. 2, 2022

(54) DETECTING AND DIAGNOSING ANOMALOUS DRIVING BEHAVIOR USING DRIVING BEHAVIOR MODELS

(71) Applicant: Byton North America Corporation, Santa Clara, CA (US)

(72) Inventors: Baharak Soltanian, Mountain View, CA (US); Divyansh Pal, Milpitas, CA (US); Enrique Israel Hernandez, San Jose, CA (US); Fangming Ye, San Jose, CA (US); Fei Xiao, San Jose, CA (US); Jian Wang, Milpitas, CA (US); Xiao Liu, Menlo Park, CA (US); Yan Deng, San Jose, CA (US)

( * ) Notice: Subject to any disclaimer, the term of this patent is extended or adjusted under 35 U.S.C. 154(b) by 0 days.

(21) Appl. No.: 16/240,567

(22) Filed: Jan. 4, 2019

(65) Prior Publication Data
US 2020/0216080 A1 Jul. 9, 2020

(51) Int. Cl.
*B60W 40/09* (2012.01)
*G06K 9/00* (2006.01)
(Continued)

(52) U.S. Cl.
CPC ............. *B60W 40/09* (2013.01); *G06N 20/00* (2019.01); *G06V 20/597* (2022.01); *G07C 5/008* (2013.01); *H04L 67/10* (2013.01)

(58) Field of Classification Search
None
See application file for complete search history.

(56) References Cited

U.S. PATENT DOCUMENTS

| 2007/0109106 A1 | 5/2007 | Maeda |
| 2011/0130916 A1 | 6/2011 | Mayer |

(Continued)

FOREIGN PATENT DOCUMENTS

| CN | 104463244 A | 3/2015 |
| CN | 105046765 A | 11/2015 |

(Continued)

OTHER PUBLICATIONS

Non-final office action dated Nov. 4, 2019 in U.S. Appl. No. 16/240,535, filed Jan. 4, 2019.
(Continued)

*Primary Examiner* — Thomas S McCormack
(74) *Attorney, Agent, or Firm* — Womble Bond Dickinson (US) LLP

(57) ABSTRACT

Embodiments and examples are disclosed for intelligent vehicle diagnostics using driving behavior modeling and monitoring. For one example, a data processing system for a vehicle includes a plurality of sensors and a vehicle control unit (VCU). The VCU may sample the output from each of the plurality of sensors and assemble a dataset which may be transmitted to a cloud computing center. The cloud computing center may apply statistical machine learning algorithms to the dataset and training data to develop a model of a user's expected driving behavior. The cloud computing center may transmit the model to the vehicle, wherein the VCU may utilize the model to monitor the user's driving behavior. In response to detecting driving behavior that is anomalous to the expected driving behavior, the VCU may diagnose the cause of the anomalous behavior and take one or more preventative actions based on the diagnosis.

27 Claims, 7 Drawing Sheets

(51) Int. Cl.
*G07C 5/00* (2006.01)
*H04L 29/08* (2006.01)
*G06N 20/00* (2019.01)
*H04L 67/10* (2022.01)
*G06V 20/59* (2022.01)

(56) References Cited

U.S. PATENT DOCUMENTS

| | | | |
|---|---|---|---|
| 2014/0226010 A1* | 8/2014 | Molin | G06Q 10/06 348/148 |
| 2015/0046046 A1 | 2/2015 | Muetzel | |
| 2017/0093866 A1 | 3/2017 | Ben-Noon | |
| 2018/0113458 A1 | 4/2018 | Dong | |
| 2018/0253963 A1* | 9/2018 | Coelho de Azevedo | G08G 1/012 |
| 2018/0255082 A1 | 9/2018 | Ostergaard | |
| 2018/0362031 A1 | 12/2018 | Chang et al. | |
| 2019/0299877 A1 | 10/2019 | Saito et al. | |

FOREIGN PATENT DOCUMENTS

| | | |
|---|---|---|
| CN | 105050868 A | 11/2015 |
| CN | 105389984 A | 3/2016 |
| CN | 106184068 A | 12/2016 |
| CN | 106203626 A | 12/2016 |
| CN | 106781581 A | 5/2017 |
| CN | 107948172 A | 4/2018 |
| CN | 108549943 A | 9/2018 |
| JP | 2009154675 A | 7/2009 |

OTHER PUBLICATIONS

The International Search Report and Written Opinion of the International Searching Authority for PCT Application No. PCT/CN2019/130615, dated Mar. 26, 2020, 8 pages.
The Notice of Allowance for U.S. Appl. No. 16/240,535 dated May 6, 2020, 20 pages.
The International Search Report and Written Opinion of PCT Application No. PCT/CN2019/130610, dated Apr. 7, 2020, 8 pages.
The Notice of Allowance for U.S. Appl. No. 16/240,535 dated Aug. 25, 2021, 16 pages.
The Notice of Allowance for U.S. Appl. No. 16/240,535 dated Apr. 20, 2021, 16 pages.
The Notice of Allowance for U.S. Appl. No. 16/240,535 dated Dec. 30, 2020, 16 pages.
The International Preliminary Report on Patenability for PCT Application No. PCT/CN2019/130610 dated Jun. 16, 2021, 5 pages.
The International Preliminary Report on Patenability for PCT Application No. PCT/CN2019/130615 dated Jun. 16, 2021, 5 pages.
Notice of Abandonment dated Dec. 10, 2021 from U.S. Appl. No. 16/240,535, 1 page.

* cited by examiner

DETECTING AND DIAGNOSING ANOMALOUS DRIVING BEHAVIOR USING DRIVING BEHAVIOR MODELS

FIELD

The disclosed embodiments relate generally to intelligent vehicle diagnostics, and more particularly to diagnostics using driving behavior modeling, analysis, and monitoring.

BACKGROUND

Vehicles have become more sophisticated with advanced electronics and integrated sensors enhancing the driving experience. Such technology allows for monitoring of various components within the vehicle, as well as the driver themselves. In addition, enhanced computer vision techniques allow vehicles to more intelligently observe their surroundings. With the complexity of modern vehicles, detecting the cause of erratic or unstable driving behavior can be difficult. Many current systems are capable of detecting when a component has failed, but not when there is a potential for failure, or that a component is close to failing such that it impacts a vehicle's driving behavior. Further, current systems may not be able to discern when a user's emotional or physical state is the cause or part of the cause of erratic driving behavior. As a result, drivers often do not know about a problem until there has been a full component failure.

SUMMARY

Embodiments of an apparatus for intelligent vehicle diagnostics using driving behavior modelling and monitoring are described. For one example, a data processing system for a vehicle includes a plurality of components, a plurality of sensors, and a computer. The computer samples the inputs from each of the sensors and generates a dataset. The computer then transmits the dataset to a cloud computing center for processing. The computer receives a model of the user's expected driving behavior and uses the model to monitor the user's current driving behavior. When driving behavior inconsistent with the expected driving behavior (as defined by the model) is detected, the computer may determine a cause of the anomalous driving behavior. Once the cause is determined, the computer may take one or more preventative actions based on the determined cause.

For one example, the computer may initiate a driver assistance protocol, and pull the vehicle over to the side of the road and/or notify emergency services. The computer can also schedule a service appointment, and order replacement parts. For one example, the user is a driver of the vehicle.

In another example, a cloud computing center may receive a dataset including a sampled output from a plurality of components. The cloud computing center may integrate the received dataset with training data from a plurality of other users, and apply statistical learning algorithms to the aggregate dataset to generate a model of the user's expected driving behavior. The cloud computing center may transmit the model to the vehicle for use in monitoring the user's driving behavior for anomalous driving behavior. For each additional dataset received from the vehicle, the cloud computing center may update the model using recursive neural network techniques and transmit the updated model to the vehicle.

Other methods and systems for expected driving behavior modeling and monitoring are described.

BRIEF DESCRIPTION OF THE DRAWINGS

The appended drawings illustrate examples and are, therefore, exemplary embodiments and not considered to be limiting in scope.

DETAILED DESCRIPTION

Embodiments and examples are disclosed for intelligent vehicle diagnostics using driving behavior modeling and monitoring. For one example, a data processing system for a vehicle includes a plurality of sensors and a vehicle control unit (VCU). The VCU may sample the output from each of the plurality of sensors and assemble a dataset which may be transmitted to a cloud computing center. The cloud computing center may apply statistical machine learning algorithms to the dataset and training data to develop a model of a user's expected driving behavior. The cloud computing center may transmit the model to the vehicle, wherein the VCU may utilize the model to monitor the user's driving behavior. In response to detecting driving behavior that is anomalous to the expected driving behavior, the VCU may diagnose the cause of the anomalous behavior and take one or more preventative actions based on the diagnosis.

Figure 1:
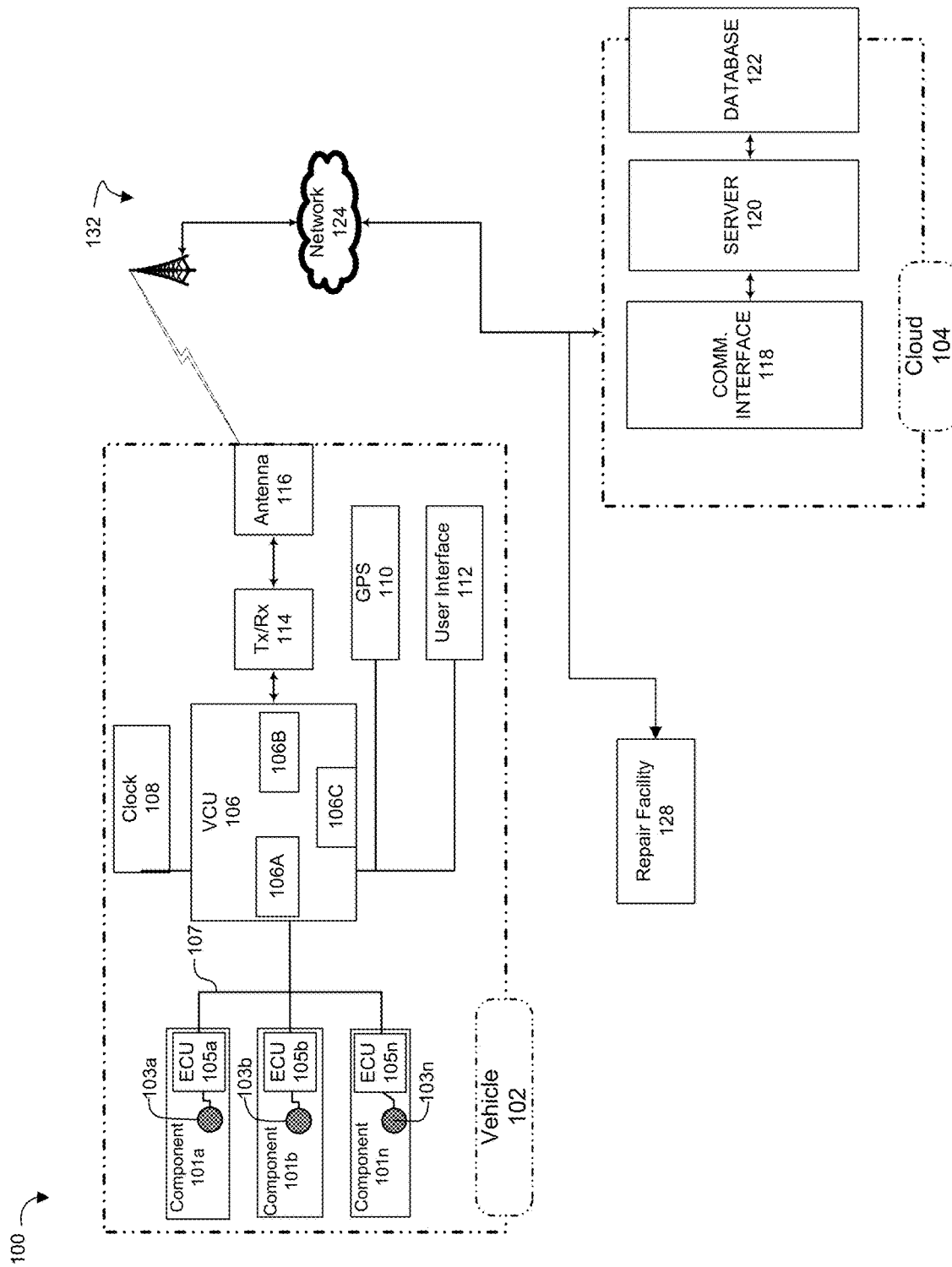
FIG. 1 illustrates a block diagram of a system in accordance with some embodiments of the present disclosure.

FIG. 1 illustrates an embodiment of a system 100 for real-time driving behavior modeling and monitoring. System 100 may implement a driving behavior analysis method so that vehicles can notify drivers of anomalous driving behavior and identify a cause of such behavior. In addition, in the case of a potential or actual component failure, the vehicle repair facility can receive corresponding component orders and maintenance requests so that they can prepare in advance to replace or repair the component. The embodiments below may be used in any appropriate vehicle, including electric, partially electric (i.e., hybrid), and non-electric vehicles, such as vehicles with a traditional internal combustion engine. The illustrated systems and methods can also be used in non-wheeled vehicles such as ships, airplanes (powered or gliders), and rockets. In fact, the illustrated embodiments can be used in any situation in which it is useful to monitor the behavior of a vehicle and detect driving behavior that is anomalous to the expected driving behavior.

System 100 includes a vehicle 102 communicatively coupled a cloud computing center 104 as well as a repair facility 128. In the context of this application, "communicatively coupled" means coupled in such a way that data can be exchanged, in one or both directions, between two entities or components. Although only one vehicle 102 is shown, in other embodiments there need not be a one-to-one correspondence between vehicles and cloud computing center 104. In other embodiments, for instance, cloud computing center 104—which can, for instance, be set up and run by a vehicle manufacturer—can be communicatively coupled to multiple vehicles from that manufacturer, up to and including the entire fleet of that manufacturer's vehicles. And although only one repair facility 128 is shown, in other embodiments vehicle 102 can be communicatively coupled to multiple repair facilities.

Vehicle 102 includes a plurality of components 101a-n, each having a sensor 103a-n and an electronic control unit (ECU) 105a-n coupled to it. Sensor 103a is coupled to component 101a, sensor 103b is coupled to component 101b, and so on. Although illustrated in the drawing as a single unit, each sensor 103a-103n can include multiple sensors, so that there need not be a one-to-one correspondence between sensors and components. In addition, some of the sensors 103a-n may not be coupled to a component 101a-n, but may be stand-alone sensors such as a LIDAR, radar, or facial and gesture recognition cameras as discussed in further detail herein. Each ECU 105a-n is communicatively coupled, via a controller area network (CAN) bus 107, to a sensor 103a-n and the vehicle control unit (VCU) 106. VCU 106 is in turn communicatively coupled to a clock 108, a GPS unit 110, a user interface 112, and a transceiver 114. Although described with respect to a CAN bus, any appropriate bus protocol may be used. Although shown in the figure as a separate component from VCU 106, for some embodiments clock 108 can be a real-time application-specific integrated circuit (ASIC) clock within VCU 106. Transceiver 114 is communicatively coupled to an antenna 116, through which vehicle 102 can wirelessly transmit data to, and receive data from, cloud computing center 104. In the illustrated embodiment, vehicle 102 communicates wirelessly via antenna 116 with a tower 132, which can then communicate via network 124 with cloud computing center 104. Sensors 103a-n may include for example, a LIDAR sensor, Radar sensor, one or more cameras, acceleration and velocity sensors, brake sensor, steering wheel position sensor, torque sensor, tire pressure monitor, inertial measurement unit (IMU) sensor, and a temperature sensor among many others. In addition, sensors 103a-n may include one or more facial recognition cameras and gesture recognition cameras (discussed with respect to FIG. 2)

Vehicle control unit (VCU) 106 is a controller including a microprocessor, memory, storage, and a communication interface with which it can communicate with components 101a-n, clock 108, global positioning system (GPS) 110, user interface 112, and transceiver 114. For one embodiment VCU 106 is the vehicle's main computer, but in other embodiments it can be a component separate from the vehicle's main or primary computer. For some embodiments, VCU 106 may be decentralized and implemented as multiple controllers that each manage a separate task. For example, one controller may manage the functions of the chassis, including for example vehicle dynamics sensors and actuators for brakes among others. Another controller may manage the functions of the power-train, including for example controlling acceleration, de-acceleration, energy regeneration commands, comfort braking, and battery charging among others. The functions of VCU 106 described herein may be distributed across one or more of these multiple controllers. VCU 106 may include an anomaly detection module 106A, a car malfunction detection component 106B, and a car intrusion detection component 106C. The car malfunction detection component 106B may include an on-board diagnostic system (not shown) for identifying component malfunctions that have manifested themselves. The on-board diagnostic system may use a diagnostic trouble code (DTC) list to identify and report components that are currently malfunctioning.

Cloud computing center 104 includes a communication interface 118, a server 120 and one or more databases 122. Communication interface 118 is communicatively coupled to server 120 and to network 124 so that cloud computing center 104 can exchange data with vehicle 102 through network 124. Although illustrated as a single server, in other embodiments server 120 can include multiple servers, each of which includes one or more microprocessors, memory, and storage.

The computational complexity and massive data storage associated with determining a model of a user's driving behavior is better implemented using cloud computing instead of the vehicle's own VCU or other onboard computational resources. Precious onboard computational resources, executive time of the microcontroller, and cost, can be saved. And because behavioral data for each component of the vehicle can be gathered in the cloud, the statistical information gathered for each component may be continuously updated and analyzed.

In addition, by generating the model in the cloud, but transmitting the model back to the vehicle for monitoring and detecting anomalous driving behavior, the vehicle does not need to rely on a 5G or similar connection with a cloud computing center to perform driving behavior monitoring.

Figure 2:
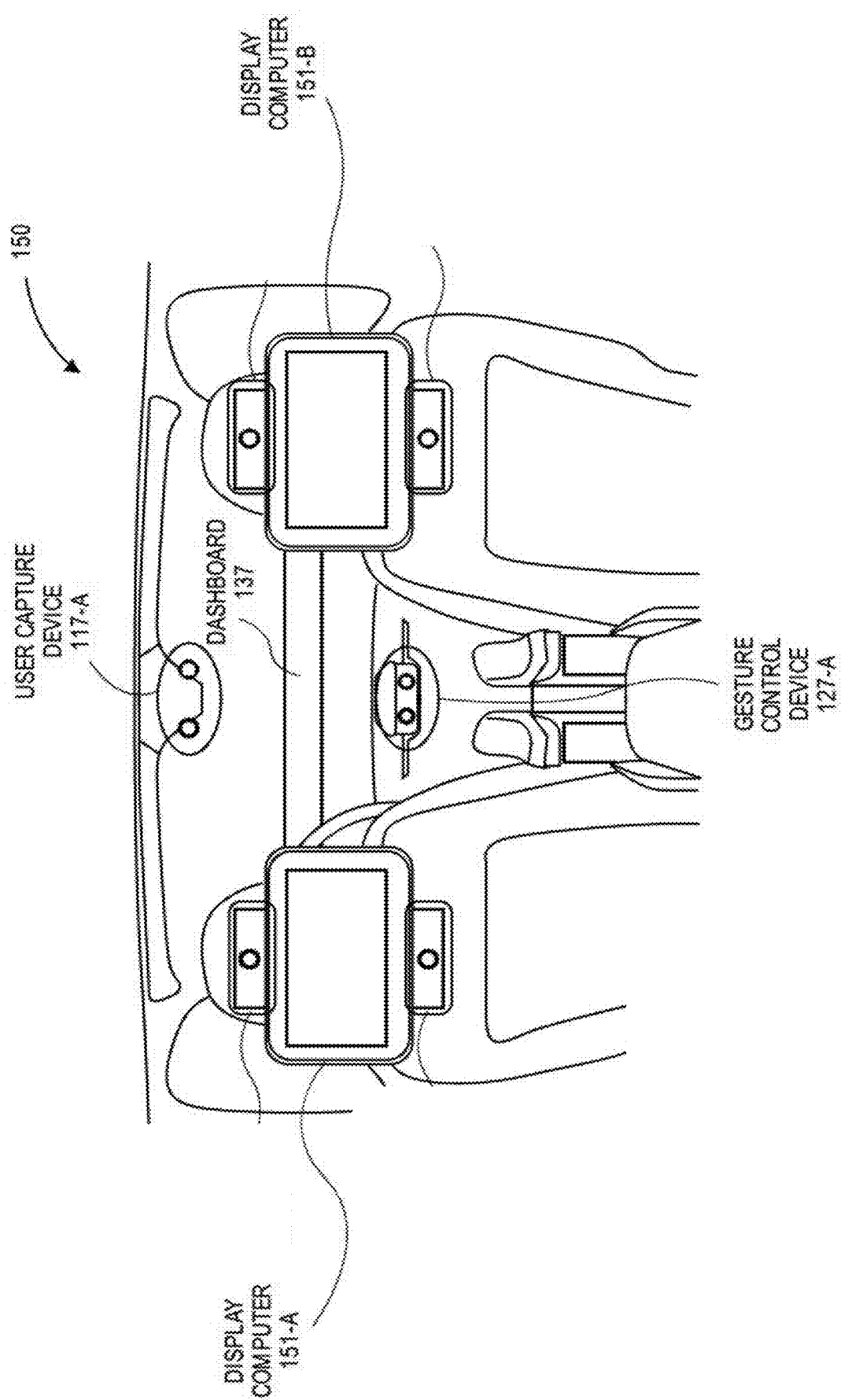
FIG. 2 illustrates one example of an inside view of a vehicle having user capture and gesture control devices in accordance with some embodiments of the present disclosure.

Referring to FIG. 2, the inside view 150 of vehicle 102 is shown from a backseat view perspective towards dashboard 137. For one example, the plurality of components 101a-n includes a capture device 117 and gesture control device 127. For one example, user capture device 117 is located above dashboard 137 at the top of the front windshield. User capture device 117 can include one or more stereo, RGB (red, green, blue), or infrared cameras to capture user images (e.g., user facial images, expressions, and features) or thermal differential information (e.g., temperature differential information of a user head and surrounding area).

For one example, user capture device 117 can capture a user image of a driver or passenger to identify and recognize the user as a valid user. For one example, if the user is determined to be a valid user, computing system and controls for vehicle 102 can configure settings and preferences for the user as a driver or passenger. For example, the driver may wish climate control to be cool and settings and preferences can be set based on the recognized driver. A passenger may also prefer certain music and music controls which can be set for the recognized passenger on a display in vehicle 102. For one example, only valid users that are identified as a valid driver can have access to driving controls of vehicle 102 and be able to drive vehicle 102.

For one example, user capture device 117 can capture one or more images or expressions of a user such as a selfie, smile, frown, sleeping, dozing, eyes opening and shutting, anger, happiness, sadness, fatigue, anger, stress, or shaking by the user. In some embodiments, the captured expression can be processed and analyzed by VCU 106 in providing a reaction or determining that no reaction is necessary. For example, if capture device 117 captures the user's eyes shutting for a predetermined period of time indicating the user is falling asleep, VCU 106 may react by providing an audio response such as "Tim please wake up you are falling asleep." Other reactions can include messages on a display, blinking lights on a display, changing settings and preferences, and etc. VCU 106 can be programmed to react in any desired manner and differently for each valid user of vehicle 102.

For one example, vehicle 102 includes a gesture control device 127 located below a dashboard of vehicle 102 and display computers 151-A and 151-B. Gesture control device 127 can include one or more cameras (e.g., time of flight TOF cameras) or motion sensors to detect hand gestures and movement of a user (e.g., a driver or passengers of vehicle 102) in controlling or accessing functions, applications, information, options, icons, or objects provided on a display of the dashboard of vehicle 102 or display computers 151-A and 151-B.

Figure 3:
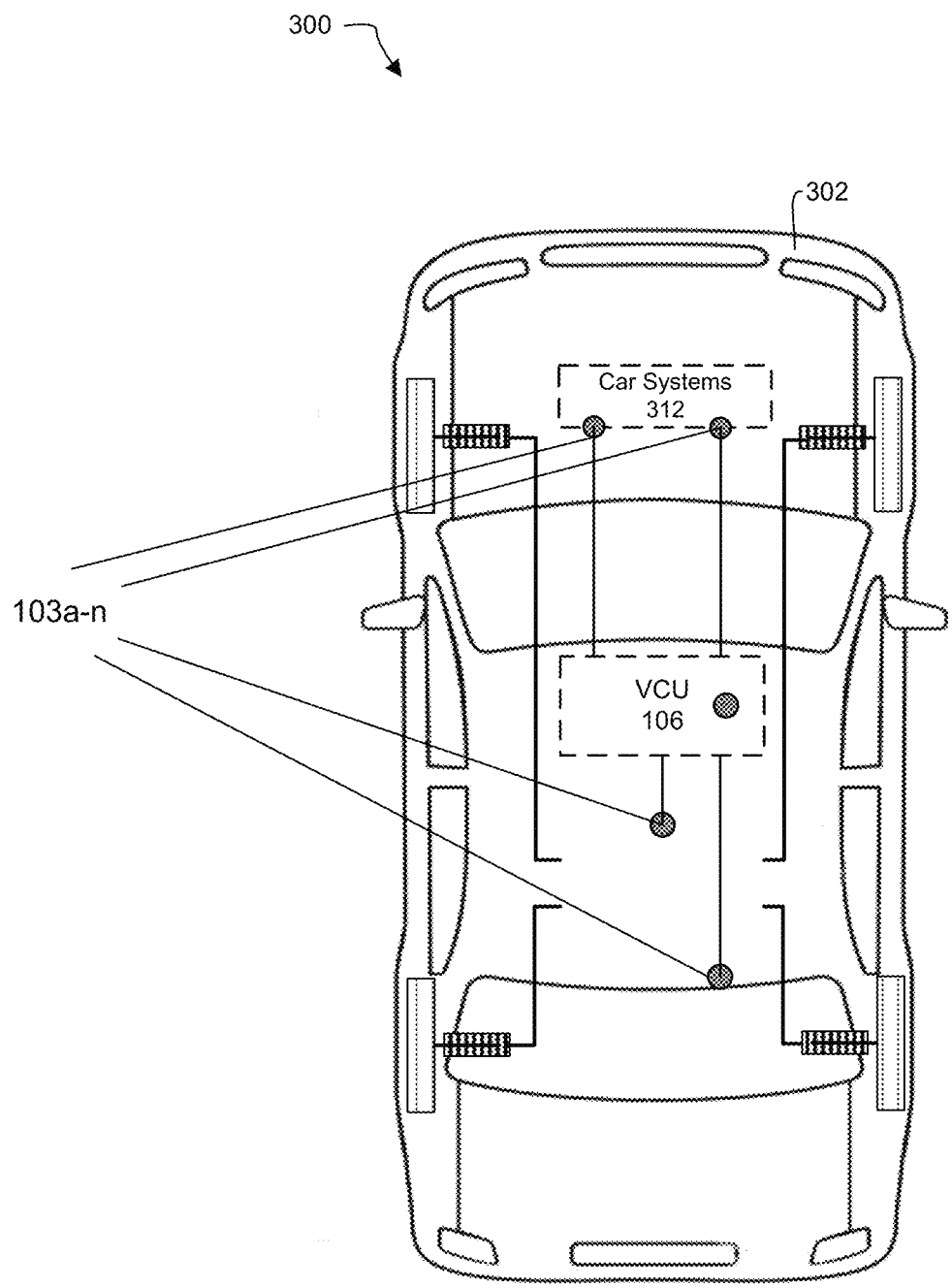
FIG. 3 illustrates a vehicle in accordance with some embodiments of the present disclosure.

FIG. 3 illustrates an embodiment of a vehicle 300 that includes an onboard driving behavior monitoring system such as shown in block-diagram form in FIG. 1. In the illustrated embodiment vehicle 300 is a passenger car, but in other embodiments it can be any another type of vehicle, such as a truck. In still other embodiments, it can be a partially electric (i.e., hybrid) vehicle or a non-electric vehicle such as a vehicle with a traditional internal combustion engine.

Vehicle 300 includes a body 302 and also includes car systems 312 which can include cooling for the car's systems such as motors, air conditioning for the vehicle cabin, gas engine control electronics (in a hybrid or internal-combustion embodiment) and other electronic components or accessories on the inside or outside of the car. A vehicle control unit (VCU) 106 is also positioned in vehicle 300. VCU 106 is communicatively coupled, via electronic control units (ECUs) within each component (not shown in FIG. 3, but see FIG. 1), to sensors 103*a*-*n* coupled to the various components 101*a*-*n* (shown in FIG. 1). For some embodiments, VCU 106 can include a sensor within itself, so that it can self-monitor.

Although not shown in FIG. 3, the other components within vehicle 102 (see FIG. 1), such as a GPS unit, a user interface, a transceiver, and an antenna, through which vehicle 300 can wirelessly transmit data to, and receive data from, a cloud computing center—will also be present in vehicle 300. Operation of the components in vehicle 300 is as described herein for FIGS. 1 and 4-7.

Figure 4:
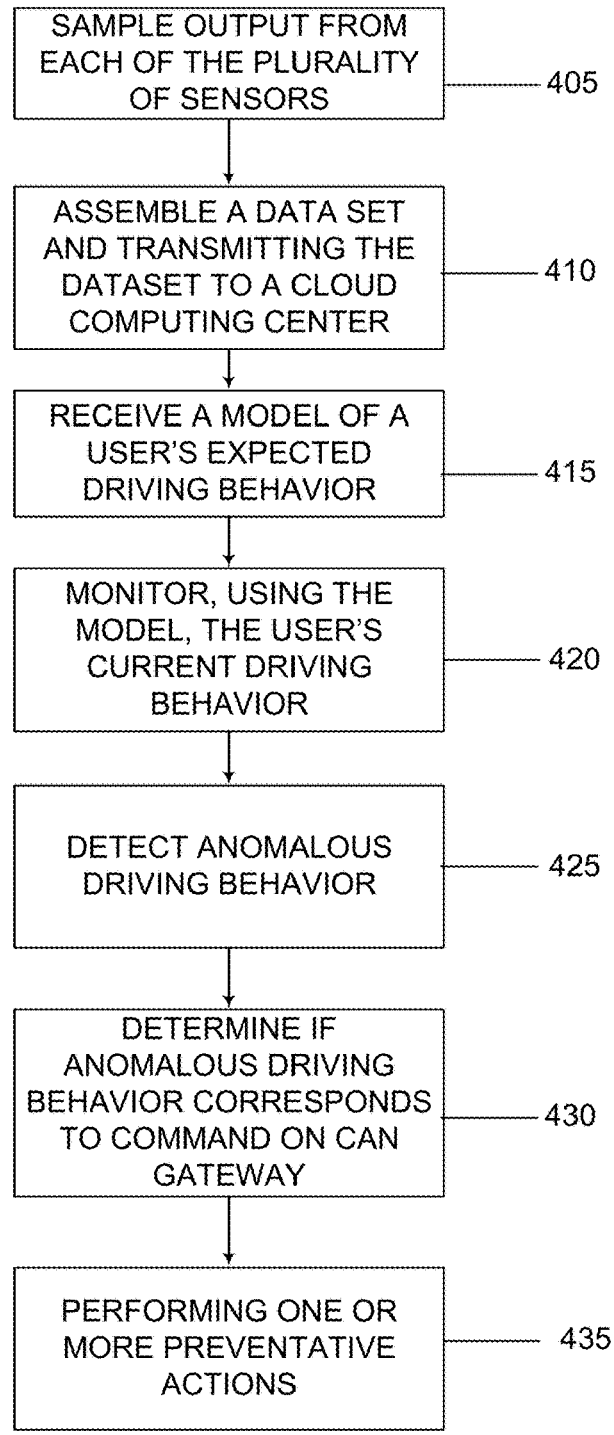
FIG. 4 illustrates a flow diagram of a method in accordance with some embodiments of the present disclosure.

FIG. 4 illustrates an embodiment of a process 400 used by a vehicle. Process 400 is discussed in the context of system 100, but can also be used in other embodiments of system 100. In system 100, process 400 is executed primarily by vehicle control unit (VCU) 106 (executing anomaly detection component 106A), but in other embodiments can be executed by a different component onboard the vehicle.

The process 400 begins at block 405, where VCU 106 samples (via ECUs 105*a*-*n*) outputs from sensors 103*a*-*n* during a reporting period—a period during which the process collects outputs for reporting to the cloud computing center 104. The reporting period and sampling frequency can be chosen so that both processes occur in real time or substantially real time. For instance, for one embodiment the reporting period and the sampling period (i.e., the reciprocal of the sampling frequency) can be equal, so that every sample is immediately transmitted to the cloud computing center. For other embodiments, the reporting period can be longer than the sampling period, so that multiple samples are aggregated before being sent to the cloud computing center 104. As discussed above, VCU 106 may sample outputs from sensors 103*a*-*n* including a LIDAR sensor, radar sensor, one or more cameras, acceleration and velocity sensors, brake sensor, steering wheel position sensor, torque sensor, tire pressure monitor, inertial measurement unit (IMU) sensor, and a temperature sensor among many others. The sampled data is sent to VCU 106 which may determine whether the reporting period has ended. If the reporting period has not ended, VCU 106 may continue to sample outputs of sensors 103*a*-*n* at the sampling frequency. Upon determining that the reporting period has ended, at block 410 the VCU 106 may assemble a dataset for transmission to cloud computing center 104. For one embodiment, the dataset may include a vehicle identifier, a sensor identifier for each sensor 103*a*-*n* whose output is being sampled, and the sampled output from each sensor. VCU 106 may transmit the dataset via transceiver 114 and antenna 116 to cloud computing center 104 for generation of a model of the user's expected driving behavior. Having transmitted the dataset to the cloud computing center 104, a new reporting period may start and the process illustrated in blocks 405-410 (sampling and transmitting outputs from the plurality of components) may continue in a repetitive fashion simultaneously with the rest of process 400.

At block 415, the vehicle 100 may receive the generated model from cloud computing system 104 via network 124. At block 420, VCU 106 may use the model to monitor the driving behavior of the user and determine whether anomalous driving behavior has been detected. For example, the model of the user's driving behavior may dynamically map the relationship between outputs from different sensors. For example, cloud computing system 104 may analyze the output from sensors such as LIDAR, radar, and one or more cameras to detect and analyze various driving scenarios (e.g., large intersections, roundabouts, stop-lights). During such scenarios, cloud computing system 104 may analyze the output from sensors such as the acceleration and velocity sensors, brake sensor, steering wheel position sensor, torque sensor, tire pressure monitor, inertial measurement unit (IMU), and a temperature sensor to determine how the driver performs and maneuvers in those scenarios. Thus, the model may form an expected behavior (i.e. output range) for each component 101*a*-*n* in various situations. For example, the model may map the relationship between acceleration in the direction of travel and braking/stopping distance. The model may also allow VCU 106 to consider tire pressure, temperature conditions, weather conditions and the driver's own braking style in determining an expected stopping distance for a particular set of speeds/conditions. If the observed stopping distance at a stop-light is different than the expected stopping distance (as prescribed by the model), then VCU 106 may consider this as anomalous driving behavior.

At block 425, VCU 106 may detect anomalous driving behavior. More specifically, VCU 106 may detect a driving behavior that is inconsistent with the expected behavior specified by the model. For example, the model may map the relationship between acceleration in the direction of travel and braking/stopping distance as well as the speed of the vehicle and steering wheel angle at roundabouts. The model may also allow VCU 106 to consider tire pressure, temperature conditions, weather conditions and the driver's own braking style in determining an expected stopping distance or turning velocity for a particular set of speeds/conditions. If the observed stopping distance at a stop-light is different than the expected stopping distance (as prescribed by the model), or the speed of the vehicle or steering wheel angle at a roundabout were beyond the expected values, then VCU 106 may consider this as anomalous driving behavior.

At block 430, the VCU 106 may compare the detected anomalous behavior to one or more commands on the CAN bus 107 to determine a cause of the inconsistency. More specifically, the VCU 106 may compare the output from each of the one or more sensors having an output inconsistent with the model to an ECU command on the CAN bus 107 in order to determine a cause of the anomalous driving behavior (as explained in further detail with respect to FIG. 6). At block 435, the VCU 106 may perform one or more preventative actions based on the determined cause of the anomalous driving behavior.

Figure 5:
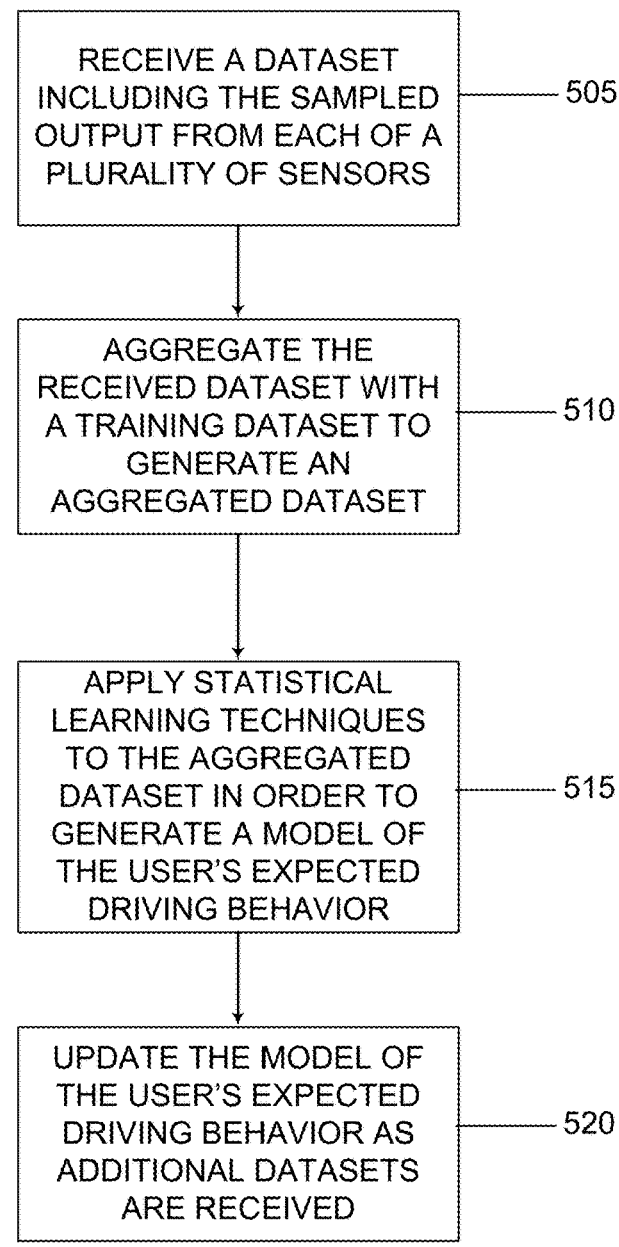
FIG. 5 illustrates a flow diagram of a method in accordance with some embodiments of the present disclosure.

FIG. 5 illustrates an embodiment of a process 500 used by the cloud computing system 104 to generate a model of the user's driving behavior based on the received data set. Process 500 is discussed in the context of system 100, but can also be used in other embodiments of system 100. Process 500 starts at block 505 where the cloud computing center 104 may receive a dataset including the sampled output from each of a plurality of sensors. At block 510, the cloud computing center 104 may aggregate the received dataset with a training dataset to generate an aggregated dataset. The training dataset may represent output values of similar sensors for a number of other vehicles. At block 515, the cloud computing center 104 may apply machine learning algorithms to the aggregated dataset in order to generate a model of the user's expected driving behavior. In some embodiments, cloud computing system 104 may utilize convolutional neural network architectures with deep learning when processing the aggregated dataset to form the model.

In some embodiments, the model may dynamically map the relationship between outputs from different sensors. For example, cloud computing system 104 may analyze the output from sensors such as LIDAR, radar, and one or more cameras to detect and analyze various driving scenarios (e.g., large intersections, roundabouts, stop-lights). During such scenarios, cloud computing system 104 may analyze the output from sensors such as the acceleration and velocity sensors, brake sensor, steering wheel position sensor, torque sensor, tire pressure monitor, inertial measurement unit (IMU) sensor, and a temperature sensor to determine how the driver performs and maneuvers in those scenarios. For example, the model may map the relationship between acceleration in the direction of travel and braking/stopping distance as well as the speed of the vehicle and steering wheel angle at roundabouts. Thus, the model may include expected outputs for each sensor during normal driving as well as driving during specific situations.

At block 520, as additional datasets are received, the cloud computing system 104 may utilize memory models such as a long-short term model with recursive neural network in order to continuously update the model of the user's expected driving behavior. The cloud computing center 104 may transmit the updated models to the vehicle 102 as they are generated.

Figure 6:
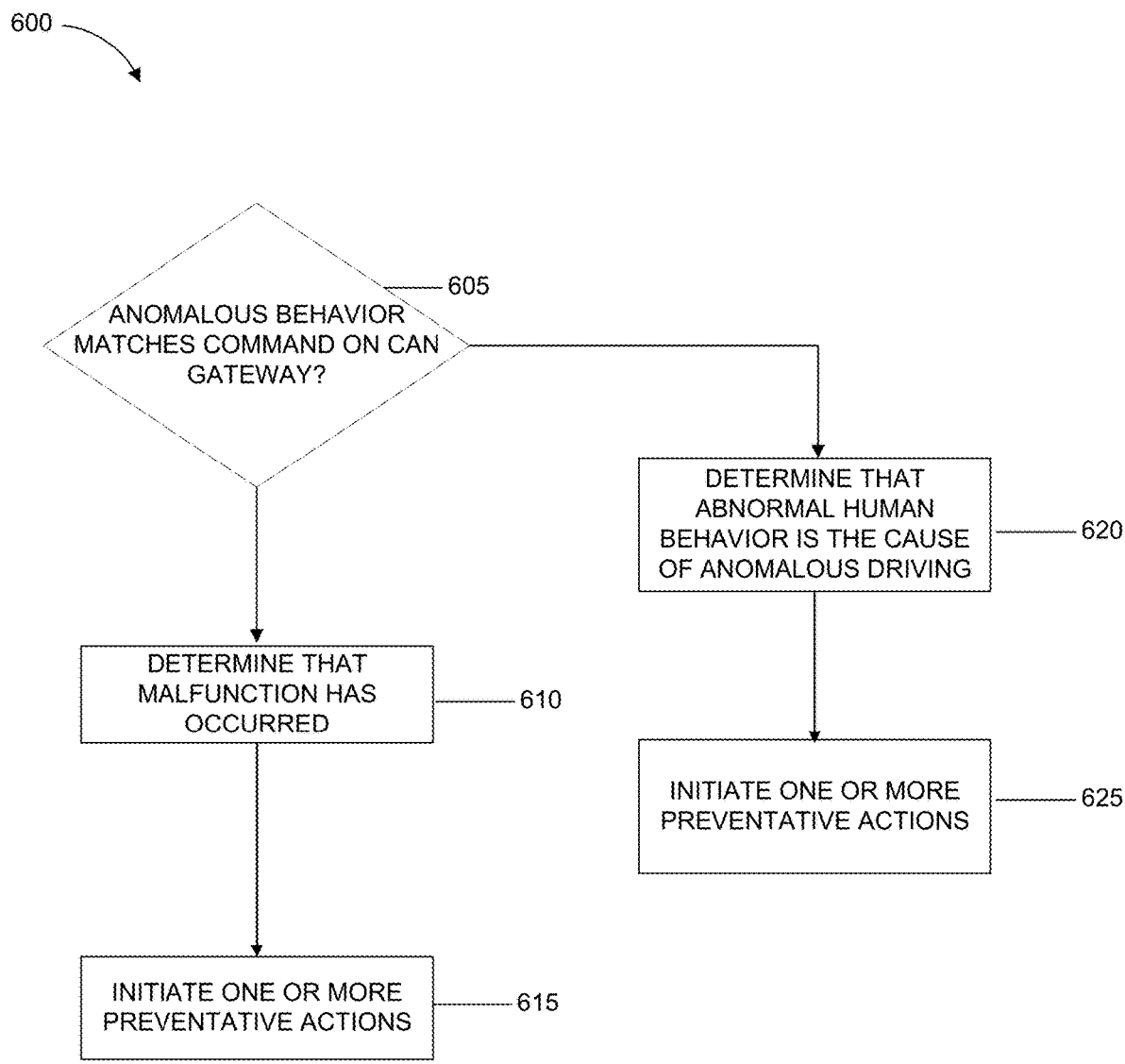
FIG. 6 illustrates a flow diagram of a method in accordance with some embodiments of the present disclosure.

FIG. 6 illustrates an embodiment of a process 600 used by a vehicle to detect malfunctioning components in a vehicle. Process 600 is discussed in the context of system 100, but can also be used in other embodiments of system 100. In system 100, process 600 is executed primarily by vehicle control unit (VCU) 106 executing malfunction detection component 106B, but in other embodiments can be executed by a different component onboard the vehicle. Process 600 starts at block 605, where upon detecting anomalous behavior (as discussed herein), the VCU 106 may compare the anomalous behavior to ECU commands that have registered on the CAN bus 107. For example, in response to the stopping distance of the vehicle exceeding an expected stopping distance (as discussed in the example above), VCU 106 may determine whether there are any commands on the CAN bus 107 (e.g., a press of the brake that was too light) that correspond to the observed braking based on the braking sensor output (i.e. did the driver purposely brake in such a way that it constituted anomalous driving behavior—in this case taking too long to stop). The process 600 includes two branches at this point, one of which may be executed in response to determining that such a command was received on the CAN bus, and one of which that may be executed in response to determining that no such command was received. At 610, in response to determining that there is no command corresponding to the anomalous driving behavior, the VCU 106 may determine that an indirect malfunction has occurred (i.e. a component is behaving abnormally and that a potential malfunction has occurred). For example, VCU 106 may determine that the brake pads are worn beyond an acceptable level. In this scenario, at block 615, the VCU 106 may initiate one or more preventative actions depending on the severity of the malfunction. For example, VCU 106 may initiate a driver assistance protocol to prevent a life-threatening scenario (e.g., using obstacle avoidance protocols) by pulling the vehicle over for example. In addition or alternatively, VCU 106 may issue a maintenance alert and/or schedule a service appointment with repair facility 128.

For some embodiments, prior to initiating preventative actions, VCU 106 may determine whether a non-malfunction type DTC alert has been triggered, and if so what the severity level of the DTC alert is. If the severity level is above a threshold, then VCU 106 may initiate a driver assistance protocol to prevent a life-threatening scenario. Otherwise the VCU 106 may issue a maintenance alert or schedule a service appointment with repair facility 128. For some embodiments, if a malfunction type DTC alert has been triggered, then VCU 106 may initiate a driver assistance protocol regardless of whether anomalous behavior has been detected. The type of driver assistance protocol initiated may depend on the severity of the malfunction.

In another example, VCU 106 may detect anomalous driving behavior as discussed herein. More specifically, VCU 106 may determine that the vehicle is moving side-to-side too much for highway driving (based for example, on input from the steering wheel angle sensor). VCU 106 may determine whether there is a corresponding command on the CAN bus 107 for such movement (i.e. did the CAN bus 107 receive a command from the steering wheel corresponding to such side to side movement). If there is not, then VCU 106 may determine that there is a malfunction in a component. VCU 106 may determine if there are any codes from the DTC list that have been triggered and may determine that the tire pressure DTC code has been activated, and that it is a malfunction type. Thus, based on the extent to which the tire is under/over pressurized, VCU 106 may issue a maintenance alert, and schedule a service to have the tire inspected/order a replacement tire, or may engage driver assistance protocols, pull the vehicle over to the side of the road and notify emergency services. Alternatively, VCU 106 may determine that there are no codes from the DTC list that have been triggered, but may determine (using the model) that the output from the tire pressure sensor is below the range of expected outputs and/or that the current tire pressure is affecting the driving dynamics of the vehicle too much. Thus, based on the extent to which the tire is under/over pressurized, and the extent to which normal driving behavior is affected, VCU 106 may issue a maintenance alert, and schedule a service to have the tire inspected/order a replacement tire, or may engage driver assistance protocols, pull the vehicle over to the side of the road and notify emergency services. For some embodiments, VCU 106 may detect that the tire pressure is inadequate (as described herein) at the outset of a trip. In this scenario, VCU 106 may obtain data from the GPS system and determine the route to the destination of the trip. VCU 106 may determine one or more service centers that are on the route and may schedule a service at a service center that is closest to the route (i.e. will require the smallest detour). For some embodiments, upon determining that the tire pressure has been reset to an appropriate level, or that a new tire has been installed on the vehicle, VCU 106 may reset the DTC code if any and ensure that the vehicle is now driving according to the model's expected driving behavior.

At block 620, in response to determining that no corresponding command was received on the CAN bus 107, the VCU 106 may determine that abnormal human behavior is the cause of the anomalous behavior and, at block 625, may initiate preventative actions such as triggering an alarm, entering driving assistance mode to prevent a life-threatening scenario (e.g., using obstacle avoidance protocols) and notifying emergency services. For some embodiments, the VCU 106 may use output from the facial and gesture recognition sensors in order to determine the appropriate preventative action. For example, in response to detecting that the user appears sleepy (detecting droopy or closed eyelids or nodding of the head), the VCU 106 may enter driving assistance mode to prevent a life-threatening scenario (e.g., using obstacle avoidance protocols) and issue an alert to wake up the user. In another example, in response to detecting that the user is not looking at the road (determining that the user's head is turned away from the road) the VCU 106 may issue an alert to remind the driver to concentrate on the road.

Figure 7:
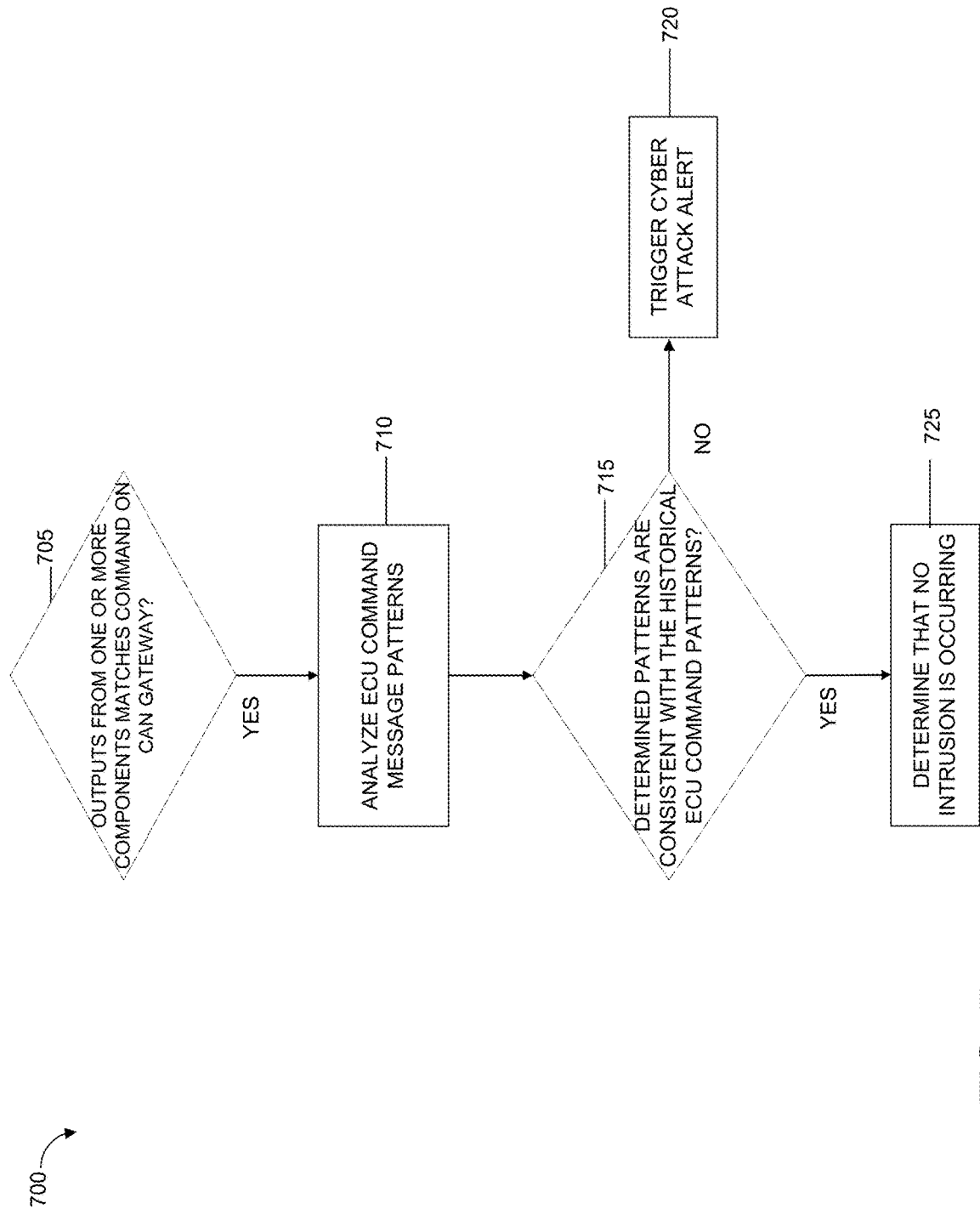
FIG. 7 illustrates a flow diagram of a method in accordance with some embodiments of the present disclosure.

For some embodiments, upon detecting anomalous driving behavior, VCU 106 may execute the intrusion detection module 106C to determine if an intrusion has occurred (e.g., vehicle 102 has been hacked into). FIG. 7 illustrates an embodiment of a process 700 used by a vehicle to detect whether the vehicle has been intruded (e.g., hacked into). Process 700 is discussed in the context of system 100, but can also be used in other embodiments of system 100. In system 100, process 700 is executed primarily by vehicle control unit (VCU) 106 (executing intrusion detection module 106C), but in other embodiments can be executed by a different component onboard the vehicle. Process 700 starts at block 705, where upon detecting anomalous behavior, the VCU 106 may compare the anomalous behavior to ECU commands that have registered on the CAN bus 107. For example, in response to the stopping distance of the vehicle exceeding an expected stopping distance (as discussed in the example above), VCU 106 may determine whether there are any commands on the CAN bus 107 (e.g., a press of the brake) that match/correspond to the observed braking (i.e. did the driver purposely brake in such a way that it constituted anomalous driving behavior—taking too long to stop). At block 710, upon determining that one or more commands on the CAN bus 107 match the detected anomalous behavior, the VCU 106 may analyze command messages issued from one or more of ECUs 105a-n and determine patterns among those ECU commands. For some embodiments, VCU 106 may only analyze command messages issued from ECUs 105a-n that correspond to components 101a-n associated with the anomalous behavior (e.g., the brake or the steering wheel). More specifically, VCU 106 may utilize a model to determine patterns among the ECU commands corresponding to the detected anomalous behavior. The model may be received from cloud computing center 104. At block 715, VCU 106 may utilize the model to compare the determined patterns to historical distributions of ECU command patterns, to analyze whether the determined patterns are consistent with the historical ECU command patterns.

The cloud computing system 104 may generate a model for detecting such attacks using a baseline of generic ECU command traffic patterns and hacker command traffic patterns. The generic and hacker traffic pattern data may be generic data generated by a third party. The data patterns of regular ECU message data and intrusion ECU message data are different because hackers usually send intrusion messages at high frequencies and within a very limited time frame (e.g., 3-10 seconds). However, ECU commands require a certain frequency and timing as well. Based on this and similar kinds of information, cloud computing center 104 may utilize particular types of machine learning models to generate models that can accurately predict these kinds of attacks based on hacker/intrusion command patterns. The cloud computing system 104 may train the model using the generic ECU command traffic patterns and hacker command traffic patterns, and further train the model using commands from the ECUs 105a-n of the vehicle 102 itself, transmitted by VCU 106 via transceiver 114 and antenna 116. In some embodiments, such command data from the vehicle may be time-series command data from ECUs 105a-n, thereby allowing the machine learning model to obtain better detection results. The cloud computing system 104 may transmit the model back to vehicle 100 via network 124.

At block 720, in response to determining that the determined patterns are not consistent with the historical ECU command patterns, VCU 106 may determine that an intrusion has occurred and send a cyber-attack alert to cloud computer system 104 and/or the dashboard of the vehicle 100. Although described with respect to CAN format commands, the process 700 is pattern based and is thus not limited to a particular bus protocol (e.g., CAN), but can be used with a variety of bus protocols such as CAN-FD and Flexray among others. In addition, many hackers attempt to use diagnostic protocols, which have their own higher-level protocol atop the underlying transport channel. However, the process 700 can be used to detect attacks carried out using diagnostic protocols as well. At block 725, upon determining that the determined patters are consistent with the historical ECU command patterns, VCU 106 may determine that no intrusion is occurring.

Those of skill would appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps or operations of a method or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

In one or more exemplary embodiments, the functions described may be implemented in hardware, software, firmware, or any combination thereof. If implemented in software as a computer program product, the functions may be stored on or transmitted over as one or more instructions or code on a non-transitory computer-readable medium. Computer-readable media can include both computer storage media and communication media including any medium that facilitates transfer of a computer program from one place to another. A storage media may be any available media that can be accessed by a computer. By way of example, and not limitation, such non-transitory computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Also, any connection is properly termed a computer-readable medium. For example, if the software is transmitted from a web site, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of non-transitory computer-readable media.

The previous description of the disclosed embodiments is provided to enable any person skilled in the art to make or use the methods, systems, and apparatus of the present disclosure. Various modifications to these embodiments will be readily apparent to those skilled in the art, and the generic principles defined herein may be applied to other embodiments without departing from the spirit or scope of the disclosure. Thus, the present disclosure is not intended to be limited to the embodiments shown herein but is to be accorded the widest scope consistent with the principles and novel features disclosed herein.

What is claimed is:

1. An apparatus comprising:
a plurality of sensors positioned in a vehicle;
a controller communicatively coupled to each of the plurality of sensors;
a transceiver communicatively coupled to the controller and to an antenna;
wherein the controller includes instructions stored thereon that, when executed by the controller, cause the controller to:
sample outputs from each of the plurality of sensors;
assemble a data set including the sampled output from each of the plurality of sensors and transmit the dataset to a cloud computing center via the antenna;
receive a model of a user's expected driving behavior;
monitor, using the model, the user's current driving behavior;
detect anomalous driving behavior based on the model;
determine whether the anomalous driving behavior has a corresponding command on a CAN bus;
responsive to determining that the anomalous driving behavior does not have a corresponding command on the CAN bus, identify a cause of the anomalous driving behavior as a component malfunction; and
perform one or more preventative actions based on the determining.

2. The apparatus of claim 1, wherein the controller is further to:
responsive to determining that the anomalous driving behavior has a corresponding command on the CAN bus, identify a cause of the anomalous driving behavior as abnormal human behavior.

3. The apparatus of claim 1, wherein the one or more preventative actions include issuing a maintenance alert, scheduling a service, and initiating a driver assistance protocol.

4. The apparatus of claim 1, wherein the one or more preventative actions include initiating a driver assistance protocol and notifying emergency services.

5. The apparatus of claim 1, wherein the model of the user's driving behavior comprises, for each of a plurality of driving scenarios, expected outputs from one or more of the plurality of sensors.

6. An apparatus, comprising:
a plurality of sensors positioned in a vehicle,
a controller communicatively couple to each of the plurality of sensors;
a transceiver communicatively coupled to the controller and to an antenna;
wherein the controller includes instructions stored thereon that, when executed by the controller, cause the controller to:
sample outputs from each of the plurality of sensors;
assemble a data set including the sampled output from each of the plurality of sensors and transmit the dataset to a cloud computing center via the antenna;
receive a model of a user's expected driving behavior;
monitor, using the model, the user's current driving behavior;
detect anomalous driving behavior based on the model;
determine whether the anomalous driving behavior has a corresponding command on a CAN bus; and
perform one or more preventative actions based on the determining, wherein the one or more preventative actions include issuing a maintenance alert, scheduling a service, and initiating a driver assistance protocol, and wherein the controller is further to:

determine that a non-malfunction direct trouble code (DTC) has been triggered; and issue the maintenance alert and schedule a service.

7. An apparatus for cloud computing, the apparatus comprising:
a communications interface;
a database; and
a server, wherein the server includes instructions stored thereon that, when executed by the server, cause the server to:
receive a dataset including a sampled output from each of a plurality of sensors on a vehicle;
develop a model of a user's expected driving behavior based, at least in part, on the sampled output from the plurality of sensors, wherein to develop the model, the server is further to apply statistical learning algorithms and convolutional neural network architectures to the received dataset, thereby dynamically mapping one or more relationships between one or more of the plurality of sensor outputs; and
transmit the model to the vehicle.

8. The apparatus of claim 7, wherein the model of the user's driving behavior comprises, for each of a plurality of driving scenarios, expected outputs from one or more of the plurality of sensors.

9. An apparatus for cloud computing, the apparatus comprising:
a communications interface;
a database; and
a server, wherein the server includes instructions stored thereon that, when executed by the server, cause the server to;
receive a dataset including a sampled output from each of a plurality of sensors on a vehicle;
develop a model of a user's expected driving behavior based, at least in part, one the sampled output from the plurality of sensors, wherein to develop the model the server is further to apply statistical learning algorithms and convolutional neural network architectures to the received dataset, thereby dynamically mapping one or more relationships between one or more of the plurality of sensor outputs; and
transmit the model to the vehicle,
wherein the server is further to:
receive a second dataset including additional sampled outputs from each of the plurality of sensors on the vehicle;
use a recursive neural network to update the model of the user's expected driving behavior based, at least in part, on the second dataset; and
transmit the updated model to the vehicle.

10. The apparatus of claim 7, further comprising aggregating the received dataset with a training dataset comprising a time-history of sampled outputs for a plurality of users.

11. A system comprising:
a vehicle comprising:
a plurality of sensors positioned in the vehicle;
a controller communicatively coupled to each of the plurality of sensors;
a transceiver communicatively coupled to the controller and to an antenna;
wherein the controller includes instructions stored thereon that, when executed by the controller, cause the controller to:
sample outputs from each of the plurality of sensors;
assemble a data set including the sampled output from each of the plurality of sensors and transmit the dataset;
receive a model of a user's expected driving behavior;
monitor, using the model, the user's current driving behavior;
detect anomalous driving behavior based on the model;
determine whether the anomalous driving behavior has a corresponding command on a CAN bus;
responsive to determining that the anomalous driving behavior does not have a corresponding command on the CAN bus, identify a cause of the anomalous driving behavior as a component malfunction; and
perform one or more preventative actions based on the determining; and
a cloud computing center comprising:
a communication interface;
one or more databases;
a server coupled to the communication interface and to the one or more databases, wherein the server includes instructions stored thereon that, when executed by the server, cause the server to:
receive the dataset including the sampled output from each of the plurality of sensors;
develop a model of a user's expected driving behavior based, at least in part, on the sampled output from the plurality of sensors; and
transmit the model to the vehicle.

12. The system of claim 11, wherein the controller is further to:
responsive to determining that the anomalous driving behavior has a corresponding command on the CAN bus, identify a cause of the anomalous driving behavior as abnormal human behavior.

13. The system of claim 11, wherein the one or more preventative actions include issuing a maintenance alert, scheduling a service, and initiating a driver assistance protocol.

14. The system of claim 11, wherein the one or more preventative actions include initiating a driver assistance protocol and notifying emergency services.

15. A system comprising:
a vehicle comprising:
a plurality of sensors positioned in the vehicle;
a controller communicatively couple to each of the plurality of sensors;
a transceiver communicatively couple to the controller and to an antenna;
wherein the controller includes instructions stored thereon that, when executed by the controller, cause the controller to:
sample outputs from each of the plurality of sensors;
assemble a data set including the sampled output from each of the plurality of sensors and transmit the dataset;
receive a model of a user's expected driving behavior;
monitor, using the model, the user's current driving behavior;
detect anomalous driving behavior based on the model;
determine whether the anomalous driving behavior has a corresponding command on a CAN bus; and perform one or more preventative actions based on the determining; and a cloud computing center comprising:
  a communication interface;
  one or more databases;
  a server coupled to the communication interface and to the one or more databases wherein the server includes instructions stored thereon that, when executed by the server, cause the server to:
    receive the dataset including the sampled output from each of the plurality of sensors;
    develop a model of a user's expected driving behavior based, at least in part, on the sampled output from the plurality of sensors, wherein to develop the model, the server is further to apply statistical learning algorithms and convolutional neural network architectures to the received dataset, thereby dynamically mapping one or more relationships between one or more of the plurality of sensor outputs; and
    transmit the model to the vehicle.

16. The system of claim 11, wherein the model of the user's driving behavior comprises, for each of a plurality of driving scenarios, expected outputs from one or more of the plurality of sensors.

17. A method comprising:
  sampling output from each of a plurality of sensors;
  assembling a data set including the sampled output from each of the plurality of sensors and transmitting the dataset to a cloud computing center;
  receiving a model of a user's expected driving behavior;
  monitoring, using the model, the user's current driving behavior;
  detecting anomalous driving behavior based on the model;
  determining whether the anomalous driving behavior has a corresponding command on a CAN bus;
  responsive to determining that the anomalous driving behavior does not have a corresponding command on the CAN bus, identifying a cause of the anomalous driving behavior as a component malfunction; and
  performing one or more preventative actions based on the determining.

18. The method of claim 17, further comprising:
  responsive to determining that the anomalous driving behavior has a corresponding command on the CAN bus, identifying a cause of the anomalous driving behavior as abnormal human behavior.

19. The method of claim 17, further comprising:
  sampling additional output from each of the plurality of sensors;
  assembling a second dataset including the additional sampled output from each of the plurality of sensors and transmitting the second dataset to a cloud computing center; and
  receiving an updated model of the user's expected driving behavior.

20. The method of claim 17, wherein the one or more preventative actions include issuing a maintenance alert, scheduling a service, and initiating a driver assistance protocol.

21. The method of claim 18, wherein the one or more preventative actions include initiating a driver assistance protocol and notifying emergency services.

22. The method of claim 17, wherein the model of the user's driving behavior comprises, for each of a plurality of driving scenarios, expected outputs from one or more of the plurality of sensors.

23. A method, comprising:
  sampling output from each of a plurality of sensors;
  assembling a data set including the sampled output from each of the plurality of sensors and transmitting the dataset to a cloud computing center;
  receiving a model of a user's expected driving behavior;
  monitoring, using the model, the user's current driving behavior;
  detecting anomalous driving behavior based on the model;
  determining whether the anomalous driving behavior has a corresponding command on a CAN bus;
  determining that a non-malfunction direct trouble code (DTC) has been triggered, and wherein the maintenance alert is issued and the service is scheduled, and
  performing one or more preventative actions based on the determining.

24. A method comprising:
  receiving a dataset including a sampled output from each of a plurality of sensors on a vehicle;
  developing a model of a user's expected driving behavior based, at least in part, on the sampled output from the plurality of sensors, wherein developing the model comprises applying statistical learning algorithms and convolutional neural network architectures to the received dataset, thereby dynamically mapping one or more relationships between one or more of the plurality of sensor outputs; and
  transmitting the model to the vehicle.

25. The method of claim 24, wherein the model of the user's driving behavior comprises, for each of a plurality of driving scenarios, expected outputs from one or more of the plurality of sensors.

26. A method, comprising:
  receiving a dataset including a sampled output from each of a plurality of sensors on a vehicle;
  developing a model of a user's expected driving behavior based, at least in part, on the sampled output from the plurality of sensors;
  transmitting the model to the vehicle;
  receiving a second dataset including additional sampled output from each of the plurality of sensors on the vehicle;
  using a recursive neural network to update the model of the user's expected driving behavior based, at least in part, on the second dataset; and
  transmitting the updated model to the vehicle.

27. The method of claim 24, further comprising aggregating the received dataset with a training dataset comprising a time-history of sample outputs for a plurality of users.

* * * * *